(12) United States Patent
Kusleika

(10) Patent No.: US 6,733,474 B2
(45) Date of Patent: May 11, 2004

(54) CATHETER FOR TISSUE DILATATION AND DRUG DELIVERY

(75) Inventor: Richard S. Kusleika, Eden Prairie, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 1 day.

(21) Appl. No.: 09/815,144

(22) Filed: Mar. 22, 2001

(65) Prior Publication Data

US 2002/0032406 A1 Mar. 14, 2002

Related U.S. Application Data

(62) Division of application No. 08/729,055, filed on Oct. 10, 1996, now abandoned.

(51) Int. Cl.[7] .............................................. A61M 31/00
(52) U.S. Cl. .................. 604/103.01; 604/523; 604/915; 604/919; 604/103.05; 604/101.02
(58) Field of Search ............ 604/96.01, 101.01–101.03, 604/102.01–102.03, 103.01, 103.02, 103.05, 103.06, 103.11–103.13, 523, 533, 915, 916, 917, 919, 104; 606/194, 191, 192

(56) References Cited

U.S. PATENT DOCUMENTS

| | | | |
|---|---|---|---|
| 4,885,003 A | * 12/1989 | Hillstead | 604/107 |
| 4,963,313 A | 10/1990 | Noddin et al. | |
| 4,994,033 A | 2/1991 | Shockey et al. | 604/101 |
| RE33,561 E | 3/1991 | Levy | |
| 5,049,132 A | 9/1991 | Shaffer et al. | 604/101 |
| 5,087,244 A | 2/1992 | Wolinsky et al. | 604/53 |
| 5,100,429 A | * 3/1992 | Sinofsky et al. | 128/DIG. 8 |
| 5,146,916 A | 9/1992 | Catalani | 128/207.14 |
| 5,176,638 A | * 1/1993 | Don Michael | 128/207.15 |
| 5,232,444 A | 8/1993 | Just et al. | |

(List continued on next page.)

FOREIGN PATENT DOCUMENTS

| | | |
|---|---|---|
| EP | 0567788 A1 | 11/1993 |
| EP | 0569263 A2 | 11/1993 |
| WO | WO91/19529 | 12/1991 |

OTHER PUBLICATIONS

"Macroporous Catheters" by Dr. Harvey Wolinsky, pp. 23.1–30.5, *JACC* vol. 24, No. 3, Sep. 1994.

"Local Drug Delivery for the Prevention of Restenosis", by Dr. A. Michael Lincoff, et al., pp. 2070–2084, *Circulation*, vol. 90, No. 4, Oct. 1994.

*Primary Examiner*—Brian L. Casler
*Assistant Examiner*—Cris L. Rodriguez
(74) *Attorney, Agent, or Firm*—Kenyon & Kenyon

(57) ABSTRACT

A combination dilatation and drug delivery device includes a flexible catheter, a drug delivery sheath mounted to a distal end region of the catheter and a dilatation balloon also mounted to the catheter and contained within a compartment formed by the sheath. The sheath is radially expandable by supplying a liquid therapeutic agent to the compartment under a moderate pressure. The dilatation balloon is expandable by providing a dilatation fluid to the balloon under a much higher pressure. The sheath can be formed of a highly elastic material or can be made quite thin, and in either case is mounted independently of the dilatation balloon. Thus when radially expanded, the sheath is moved into a conforming contact with surrounding vascular tissue. The conforming contact protects tissue and the therapeutic agent from exposure to blood, and more effectively confines the therapeutic agent to the intended treatment area. The sheath either is naturally porous or is provided with multiple pores, whereby the therapeutic agent perfuses through the sheath into the surrounding tissue.

17 Claims, 4 Drawing Sheets

U.S. PATENT DOCUMENTS

| | | | |
|---|---|---|---|
| 5,236,413 A | 8/1993 | Feiring | 604/96 |
| 5,267,959 A | 12/1993 | Forman | |
| 5,295,962 A | 3/1994 | Crocker et al. | 604/101 |
| 5,306,250 A * | 4/1994 | March et al. | 604/104 |
| 5,318,531 A | 6/1994 | Leone | 604/96 |
| 5,342,305 A | 8/1994 | Shonk | 604/101 |
| 5,358,487 A | 10/1994 | Miller | 604/96 |
| 5,415,635 A | 5/1995 | Bagaoisan et al. | 604/96 |
| 5,415,636 A | 5/1995 | Forman | |
| 5,421,826 A | 6/1995 | Crocker et al. | |
| 5,425,709 A * | 6/1995 | Gambale | 604/103.05 |
| 5,447,497 A | 9/1995 | Sogard et al. | 604/101 |
| 5,527,282 A * | 6/1996 | Segal | 604/104 |
| 5,569,184 A * | 10/1996 | Crocker et al. | 604/103.01 |
| 5,609,574 A * | 3/1997 | Kaplan et al. | 604/103.02 |
| 5,611,775 A | 3/1997 | Machold et al. | 604/53 |
| 5,807,306 A * | 9/1998 | Shapland et al. | 604/21 |
| 5,840,076 A * | 11/1998 | Swanson et al. | 606/34 |
| 5,868,704 A * | 2/1999 | Campbell et al. | 604/103.11 |
| 5,873,811 A * | 2/1999 | Wang et al. | 600/3 |

* cited by examiner

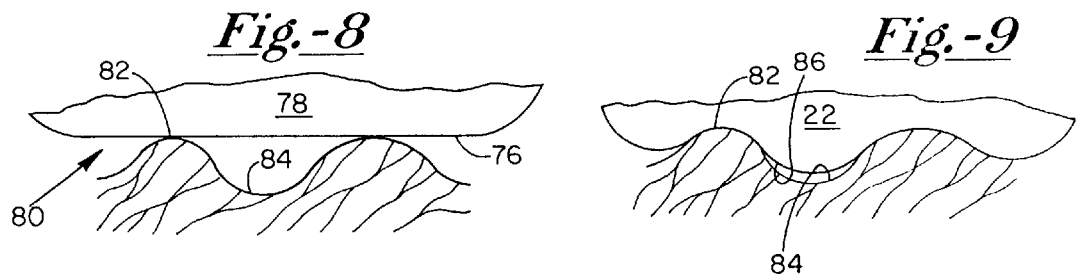
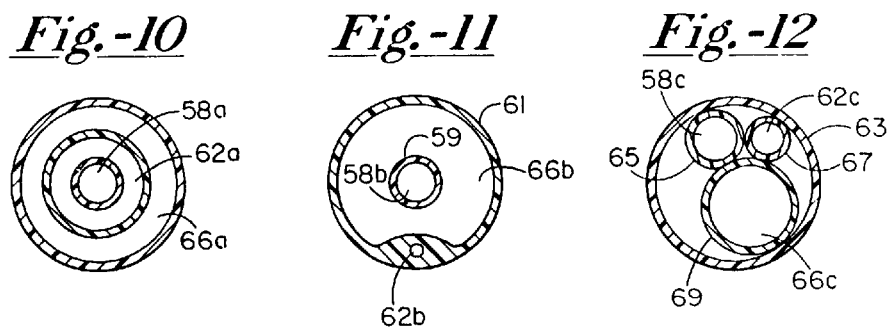
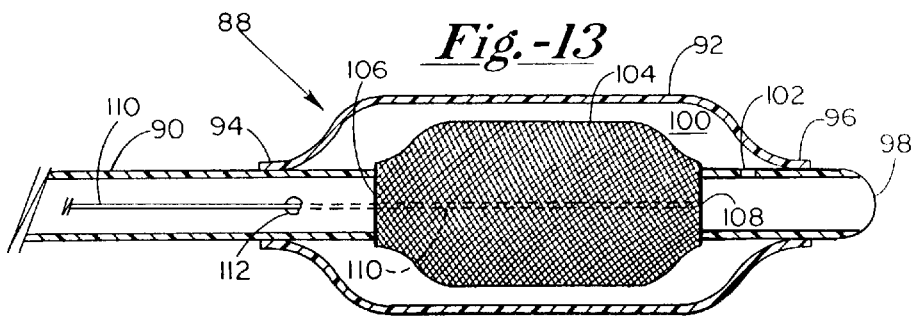

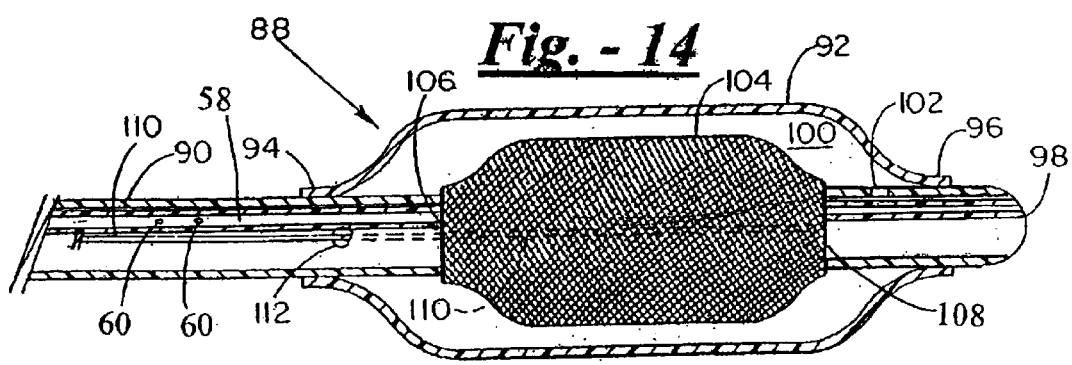

CATHETER FOR TISSUE DILATATION AND DRUG DELIVERY

This application is a Divisional Application of U.S. patent application Ser. No. 08/729,055, filed Oct. 10, 1996, now abandoned and entitled "CATHETER FOR TISSUE DILATATION AND DRUG DELIVERY".

BACKGROUND OF THE INVENTION

The present invention relates to devices used in percutaneous transluminal angioplasty (PTA) and percutaneous transluminal coronary angioplasty (PTCA) procedures, particularly when adapted for the dilatation of intravascular tissue and the localized delivery of a therapeutic agent to the dilatated tissue.

PTA and PTCA procedures have gained widespread acceptance in the treatment of vascular constrictions and blockages, and are increasingly favored because they involve less trauma and lower cost compared to traditional alternative procedures such as coronary bypass. However, the recurrence of total or partial blockage, usually from three to six months after the procedure, continues to be of concern. This phenomenon, known as restenosis, appears in about thirty percent or more of the cases that originally appear successful. Restenosis can present a risk to the patient and typically necessitates another tissue dilatation, or an alternative procedure.

Certain therapeutic agents can be administered to reduce restenosis, e.g. anti-thrombolitic agents such as heparin to prevent clotting, and anti-proliferative agents such as dexamethasone to prevent smooth muscle cell migration and proliferation. Catheters have been developed for local delivery of therapeutic agents. For example, U.S. Pat. No. 5,087,244 (Wolinsky) discloses a catheter with a substantially inelastic distal balloon with a plurality of minute (e.g. 25 micrometer) perforations said to provide a low, weeping flow rate of a liquid to the surrounding tissue. Another approach to localized delivery involves inflating spaced apart proximal and distal balloons against arterial walls to provide a chamber about a treatment site, then delivering an agent into the chamber, e.g. as disclosed in U.S. Pat. No. 4,824,436 (Wolinsky).

Several devices have been developed to perform both the dilatation and drug delivery functions. Examples include U.S. Pat. No. 5,415,636 (Forman), assigned to the assignee of this application, featuring a catheter with a dilatation balloon and a pair of occlusion balloons, one proximal and one distal with respect to a drug delivery port. U.S. Pat. No. 4,994,033 (Schockey), also assigned to the present assignee, discloses an intravascular dilation and delivery catheter with inner and outer hollow expansible sleeves at the distal ends of three concentric catheters. The outer sleeve includes minute openings through which a liquid dispersant perfuses as the inner sleeve is expanded.

U.S. Pat. No. 5,049,132 (Shaffer) discloses a two-balloon catheter in which the outer balloon includes apertures sized to permit flow of a liquid through the balloon to treat tissue, and in which the outer balloon is spot-sealed to an inner balloon in several areas spaced from the ends of the balloons. In U.S. Pat. No. 5,421,826 (Crocker) a drug delivery balloon with perforations is disposed concentrically about a dilatation balloon, with the two balloons preferably heat sealed together at the proximal and distal ends. The dilatation balloon is used to expel the drug out of the drug delivery balloon, and pulls the delivery balloon with it when aspirated, to minimize external dimensions.

The aforementioned approaches have proven useful in certain circumstances. However, the growing interest in gene therapy for treating cardiovascular diseases including restenosis, and the nature of coronary arteries, raise challenges not yet adequately addressed.

More particularly, gene therapy involves large, complex molecules that tend to rapidly combine with proteins in the bloodstream to lose their efficacy. This raises a need to protect gene therapy agents from contact with the blood as they are maintained in contact with a vessel wall under treatment. Similarly, a freshly cracked lesion can be more effectively medicated if it is protected from contact with blood during treatment.

Coronary vasculature includes many collateral arteries and branches in which the conventional two-balloon approach does not effectively block or divert the flow of blood, nor do the conventional non-distensible dilatation and drug delivery balloons establish a conforming contact with the arterial wall at low pressures.

Therefore, it is an object of the present invention to provide a drug delivery device for effectively maintaining a therapeutic agent in contact with vessel walls while protecting the vessel walls and the agent from contact with blood.

Another object is to provide a combination tissue dilatation and drug delivery device that facilitates substantially immediate treatment of a freshly cracked lesion while protecting the lesion from contact with blood.

A further object is to provide a process for treating vascular tissue including expanding a liquid permeable sheath elastically into intimate and substantially conforming contact with the vascular tissue, and causing a therapeutic agent to pass through the sheath to the surrounding tissue while the sheath remains expanded.

Yet another object is to provide a dilatation and drug delivery device in which a therapeutic agent is administered after tissue dilatation and at a pressure and flow rate determined independently of the tissue dilatation means.

SUMMARY OF THE INVENTION

To achieve the above and other objects, there is provided a body insertable treatment device. The device includes an elongate delivery member having a proximal end region and a distal end region. The delivery member is maneuverable transluminally to position the distal end region at a treatment site within the body lumen. The device has a treatment fluid delivery means including a sheath mounted to the delivery member along the distal end region. The sheath is elastically expandable radially into a substantially conforming contact with surrounding tissue at the treatment site. While expanded, the sheath provides a compartment for containing at treatment fluid. The sheath further is adapted to allow passage of the treatment fluid from within the compartment to the surrounding tissue during such contact. The treatment fluid delivery means further includes a means for supplying the treatment fluid under pressure to the compartment to expand the sheath radially into the conforming contact, to maintain such contact, and to provide the treatment fluid for such passage of the treatment fluid. A tissue dilatation means is mounted to the delivery member and disposed within the compartment. The tissue dilatation means is enlargeable to act radially upon the surrounding tissue through the sheath and thereby effect a dilatation of the surrounding tissue. The dilatation means and the sheath are mounted to the delivery member independent from one another to allow radial expansion of the sheath into the conforming contact without radially enlarging the dilatation means, and to allow radial contraction of dilatation means while maintaining the sheath in such contact.

Preferably the delivery means comprises an elongate and flexible catheter, with the dilatation means comprising a substantially inelastic and fluid impermeable dilatation balloon. The catheter has at least two lumens, one fluidly coupled to the dilatation balloon for supplying a fluid under pressure to the dilatation chamber, and the other open to the compartment for supplying the treatment fluid under pressure to expand the sheath and provide the desired treatment. A third lumen can run substantially the length of the catheter, to accommodate a guidewire.

The sheath advantageously is formed of a biocompatible elastomer having a modulus of elasticity in the range of about 2,000 to 80,000 psi, and with a uniform thickness in the range of about 0.5–5 mils. Accordingly, responsive to a low inflation pressure (e.g. about one atmosphere gauge pressure), the sheath readily expands into the desired intimate and conforming contact with tissue. The elasticity is a positive factor in permitting the sheath to stretch in response to encountering tissue surface irregularities.

The sheath material can be either fluid impervious or naturally porous. In the former case, pores are formed through the material with a size, number and arrangement as desired. In the latter case, the material is selected with the desired pore size in mind. Some of the porous materials (e.g. collagen) lack the elasticity just discussed, yet provide the necessary conforming contact if kept sufficiently thin, e.g. at most about 2 mils in thickness.

Several advantages arise from the conforming contact of the sheath against vascular tissue. The first is an improved fluid seal that more effectively prevents blood from flowing between the expanded sheath and the surrounding tissue. This protects the tissue from exposure to blood, while also protecting a therapeutic agent from such exposure during its administration. If extended treatment is contemplated, the catheter can include a perfusion lumen enabling blood to flow past the treatment area without contacting tissue under treatment.

A further advantage is a more uniform administration of the therapeutic agent. Regardless of whether the sheath is formed of a porous material, or a substantially fluid impervious material in which multiple pores are formed, improved uniformity of application results from the more intimate and more conforming surface contact. Crevices, folds and other recessive tissue irregularities are more likely to receive the therapeutic agent.

The device is particularly effective as part of a treatment system that further includes a control means to govern a first fluid pressure at which the treatment fluid is provided to the compartment, a second control means to govern a second fluid pressure at which dilatation fluid is provided to the dilatation balloon, and further includes a guidewire adapted for intravascular insertion to position a distal end of the guidewire near the treatment site and a proximal end for receipt into a distal end of the guidewire lumen, to facilitate a distal advance of the catheter over the guidewire toward the treatment site.

The system can be employed in a process for treating tissue within a body lumen, according to the following steps:

a. distally intraluminally advancing an elongate flexible catheter until a flexible sheath mounted to a distal end of the catheter is aligned with a predetermined treatment site;

b. supplying a treatment fluid under pressure to a compartment formed by the sheath, (i) to elastically expand the sheath radially into an intimate and substantially conforming contact with surrounding tissue at the treatment site, (ii) to cause the treatment fluid to pass through the sheath from the compartment to the surrounding tissue, and (iii) to maintain the sheath expanded into such contact.

The process further can include the following additional steps:

c. while maintaining the sheath in such contact, radially expanding a tissue dilatation means within the compartment until the dilatation means engages the sheath, then further radially expanding the dilatation means whereby the dilatation means acts radially upon the surrounding tissue through the sheath to effect a dilatation of the surrounding tissue;

d. following the dilatation, radially contracting the dilatation means and simultaneously maintaining the sheath in such contact to administer the treatment fluid to the dilatated tissue; and e. following said administering of the treatment fluid, discontinuing the supply of the treatment fluid to allow the sheath to radially contract under a residual elastic force.

Because the sheath is maintained in contact with tissue during dilatation, freshly created tissue surfaces are protected from contact with blood. Radial contraction of the dilatation means while maintaining the sheath in contact with tissue ensures that administration of the therapeutic agent occurs at a suitably low pressure, free from any influence due to the higher pressures characteristic of tissue dilatation balloons (e.g. 12–15 atmospheres). Thus, the present arrangement avoids two problems of prior devices that depend on dilatation balloon inflation for "squeezably" delivering drugs: (1) the tendency in irregular vessel profiles for the dilatation balloon to contact radially inward parts of the drug delivery balloon, to the point of closing off some of the drug delivery pores; and (2) unwanted pressure gradients in the treatment fluid, due to episodes and near episodes of such contact. Consequently the present arrangement affords a more uniform delivery and better control over the pressure and flow rate of the therapeutic agent.

Thus in accordance with the present invention, the likelihood of restenosis is significantly reduced due to administration of therapeutic agents through an elastic membrane held in intimate, conforming contact with the tissue under treatment. The agent is effectively concentrated at the treatment area, with little or no loss into the bloodstream and virtually no contact with blood. At the same time the tissue is protected from contact with blood during treatment.

IN THE DRAWINGS

For the further understanding of the above and other features and advantages, reference is made to the following detailed description and to the drawings, in which.

FIGS. 4–7 schematically illustrate the device employed in a treatment procedure;

FIG. 8 illustrates the substantially non-conforming surface contact of an inflated non-distensible balloon and adjacent vascular tissue;

FIG. 9 illustrates the substantially conforming surface contact of an inflated elastic drug delivery sheath and adjacent vascular tissue;

FIGS. 10–12 illustrate alternative lumen configurations; and

FIG. 13 illustrates an alternative embodiment dilatation and drug delivery device.

FIG. 14 illustrates an embodiment of a dilatation and drug delivery device including a perfusion passage.

DETAILED DESCRIPTION OF THE PREFERRED EMBODIMENTS

Figure 1:
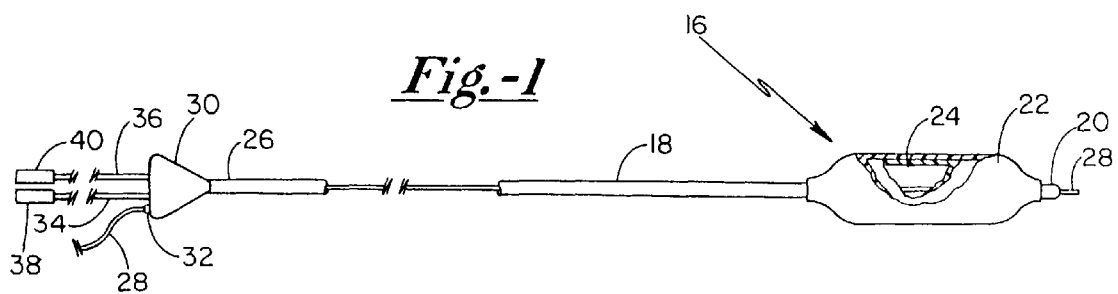
FIG. 1 is an elevational view of an intraluminal tissue dilatation and drug delivery device constructed according to the present invention.

Turning now to the drawings, there is shown in FIG. 1 an intraluminal treatment device 16 for dilatating tissue at a selected treatment site along a blood vessel or other body lumen, and for delivering a liquid therapeutic agent to tissue at the selected treatment site.

Device 16 includes an elongate and flexible catheter 18 constructed of a biocompatible thermoplastic elastomer, e.g. polyurethane or nylon, typically with an outside diameter in the range of 0.5–1.5 mm for coronary applications, in particular percutaneous transluminal coronary angioplasty. Catheter 18 can have a length in the range of 100–200 cm.

Catheter 18 has a distal end region that includes a distal tip 20. A drug delivery sheath 22 in the form of a balloon is mounted to the catheter along the distal end region. Part of sheath 22 is removed in the figure to reveal a dilatation balloon 24. The dilatation balloon, also mounted to catheter 18 along the distal end region, is contained entirely within sheath 22.

In use, device 16 is maneuvered transluminally to position the distal end region at a selected treatment site within the body, for example within a coronary artery, while a proximal region 26 of the device remains outside of the body. The device preferably is part of a system that also includes a guidewire 28 that is intraluminally positioned before insertion of the catheter. The catheter tracks the guidewire as it is advanced toward the treatment site.

A manifold 30, coupled to the proximal end of the catheter 18, includes a port 32 for accommodating guidewire 28. A dilatation fluid tube 34 and a drug delivery tube 36 are coupled to the manifold and releasably coupled to respective fluid sources 38 and 40, typically syringes. Source 38 is used to supply a balloon dilatation fluid (e.g. a saline solution) under pressure through the catheter to the dilatation balloon, thus to radially expand the balloon. Similarly, source 40 is used to supply a liquid therapeutic agent under pressure to sheath 22.

Figure 2:
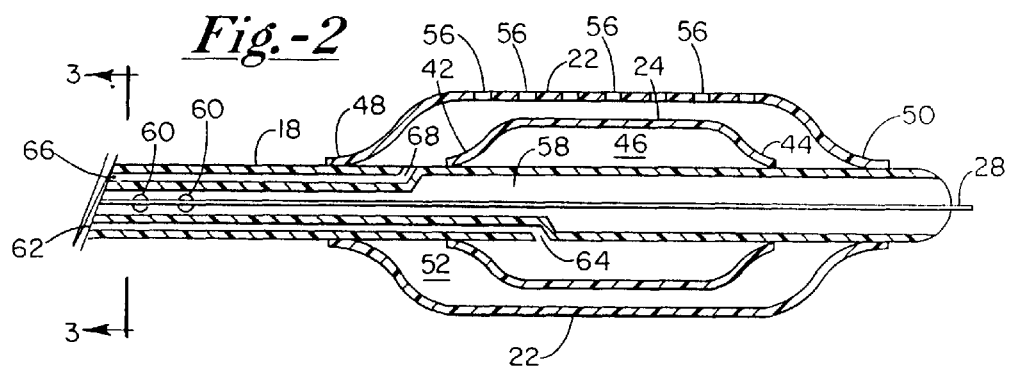
FIG. 2 is an enlarged view in section, showing a distal region of the device.

As seen in FIG. 2, dilatation balloon 24 is sealed in fluid tight fashion to catheter 18 at a proximal neck 42 and a distal neck 44, by laser bonding as disclosed in U.S. Pat. No. 5,267,959 (Forman) assigned to the assignee of this application, by fusion, or with an adhesive. The dilatation balloon and the catheter cooperate to form a dilatation chamber 46 for receiving the dilatation fluid.

A plurality of pores 56 are formed through sheath 22, throughout a medial region of the sheath and relatively remote from neck regions 48 and 50. The pores can be uniformly arranged throughout the medial region and uniform in diameter. The pore diameter is selected to achieve a predetermined rate of perfusion of a liquid therapeutic agent outwardly through the sheath in response to a moderate fluid pressure (1–2 atmospheres). For example, the pore diameter can be in the range of 15 to 100 microns, depending primarily on the viscosity of the therapeutic agent.

Dilatation balloon 24 preferably is constructed of a polymeric material that is sufficiently pliable or formable to readily achieve an enlarged state, yet is relatively non-distensible, i.e. tending to maintain it shape under increased fluid pressure within the balloon. Nylon is a preferred material for the dilatation balloon. Other suitable materials include PET, polyolefin, polyethylene, polybutylene terepthalate, PVC, polypropylene and their copolymers. Where a multilayer, coextruded dilatation balloon construction is desired, e.g. as disclosed in U.S. Pat. No. 5,270,086 (Hamlin) assigned to the assignee of this application, a preferred wall includes layers of nylon and PET.

Sheath 22 is also fastened to the catheter distal end region, in fluid tight fashion at respective proximal and distal neck regions 48 and 50. Neck region 48 is shown proximal with respect to neck 42, and neck region 50 is shown distal with respect to neck 44. Alternatively the respective necks and neck regions can overlap. In either event, the dilatation balloon and drug delivery sheath are not coupled to one another at any point between necks 42 and 44. Sheath 22 forms a compartment 52 around the sheath and dilatation balloon for receiving a liquid therapeutic agent.

Delivery sheath 22 is formed of an elastic biocompatible polymer, e.g. latex. Other suitable materials include polyurethane, silicone, and thermoplastic elastomers. The thickness of the sheath is determined in view of the selected material, to provide a high degree of stretching of the sheath to conform to the shape and contours of surrounding tissue when sheath 22 is expanded against the tissue. In general, the ability of the sheath to conform to tissue irregularities is a function of the material modulus of elasticity and sheath thickness. Consistent with an adequate tensile strength, lower elastic moduli are preferred. A sheath having a lower modulus of elasticity experiences a greater amount of elastic elongation or "stretch" in response to a given force, i.e. a given fluid pressure of the therapeutic agent in the compartment. In particular, suitable materials will have elastic moduli within a range from about 2,000 psi to about 80,000 psi. Preferred thicknesses are in the range of from about 0.5 mils to about 5 mils.

Figure 3:
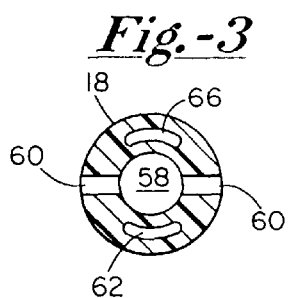
FIG. 3 is a sectional view taken along the line 3—3 in FIG. 2.

As seen in FIGS. 2 and 3, several lumens are formed within catheter 18. A central lumen 58, extending the entire length of the catheter from manifold 30 to distal tip 20, accommodates guidewire 28. Several holes 60 open to the catheter exterior and to central lumen 58 are formed proximally of neck region 48. The holes enable central lumen 58 to function as a perfusion lumen, with blood entering lumen 58 through holes 60 and flowing distally past balloon 24 and sheath 22, to exit catheter 18 at its distal end. Alternatively a separate lumen can be provided, solely for blood perfusion. While these figures illustrate an over-the-wire configuration, catheter 18 if desired can be formed with rapid exchange features, e.g. as disclosed in U.S. Pat. No. 4,762,129 (Bonzel).

A dilatation fluid lumen 62 runs proximally along the catheter from manifold 30 to a distal opening 64 in fluid communication with dilatation balloon chamber 46. Similarly, a drug delivery lumen 66 runs from manifold 30 to a distal opening 68 in fluid communication with compartment 52. Lumens 58, 62 and 66 are fluid isolated from one another.

FIGS. 4–7 illustrate use of the system that includes device 16 to treat stenosis 70 within a coronary artery 72 along an arterial wall 74.

Figure 4:
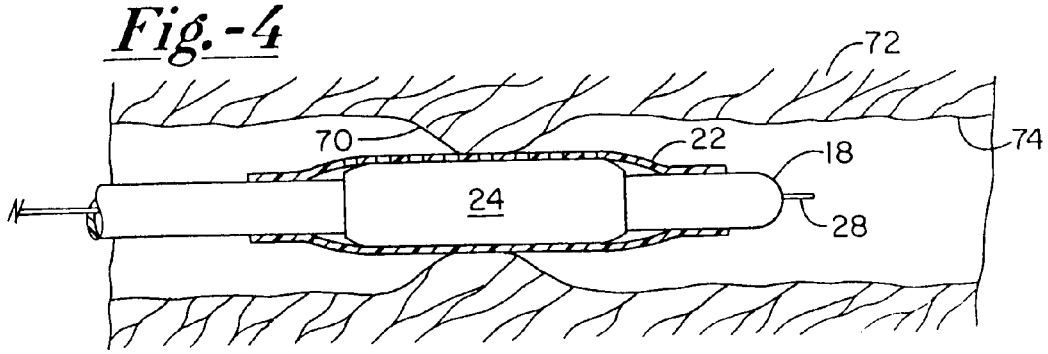

The procedure begins with the intraluminal positioning of guidewire 28, to locate its distal end just beyond the selected treatment site, i.e. the stenosis. A steerable guidewire catheter (not shown) can be used for this purpose, or the guidewire itself can be steerable. With guidewire 28 in place, catheter 18 is advanced distally over the guidewire, to track the guidewire through vasculature until it reaches the treatment site as seen in FIG. 4. At this point guidewire 28 may be proximally withdrawn. Alternatively, if the procedure involves use of another treatment device, guidewire 28 remains in place for the required exchange.

Figure 5:
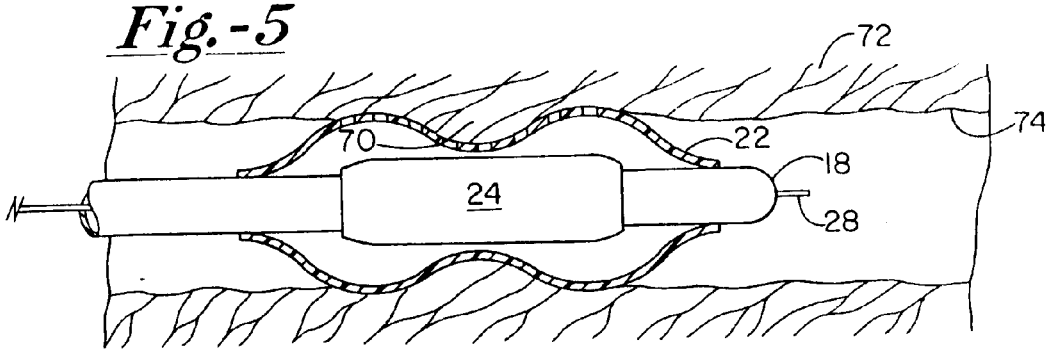

With the distal region of catheter 18 aligned with occlusion 70 as shown, syringe 40 is used to supply a therapeutic agent under pressure to compartment 52 via lumen 66. The pressurized fluid expands drug delivery sheath 22, radially, into contact with arterial wall 74 and more specifically with the tissue forming partial occlusion 70. Because of the elasticity of sheath 22, it does not enlarge the artery or otherwise substantially change the shape of the surrounding tissue. Rather, it conforms to the shape and contours of the vessel wall, as seen in FIG. 5. At this stage, the therapeutic agent perfuses through pores 56 and is applied directly to the arterial tissue wherever sheath 22 and the tissue are contiguous. Because pores 56 are located largely in the medial region of sheath 22 rather than near the neck regions, loss of the therapeutic agent to the bloodstream is minimal and the agent is concentrated along the intended treatment area. The pressure required for expanding sheath 22 is moderate due to the balloon elasticity, e.g. less than about 6 atmospheres, and more preferably in the range of 1–2 atmospheres.

Figure 6:
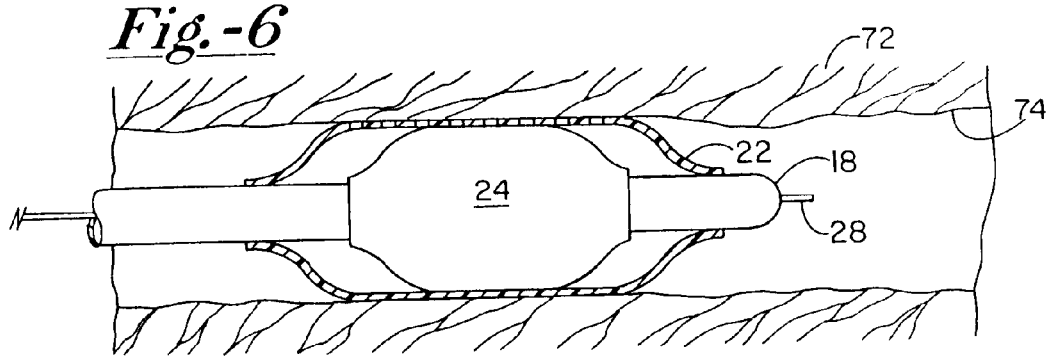

Next, while delivery sheath 22 is maintained in the radially expanded state, syringe 38 is used to supply a dilatation fluid, usually a contrast medium diluted 1:1 with heparinized saline, to chamber 46 via lumen 62. This expands dilatation balloon 24. The dilatation balloon is non-distensible and expanded under a relatively high pressure, e.g. 12–15 atmospheres. As a result, balloon 24 when expanded radially does not conform to the shape and contours of the arterial tissue. Rather, balloon 24 acts upon the arterial tissue through sheath 22, compressing the partial occlusion to enlarge the artery as shown in FIG. 6. With dilatation balloon 24 pressed against sheath 22, perfusion of the agent through the sheath into surrounding tissue may be substantially reduced or even interrupted. At other locations the dilatation balloon may tend to squeeze the therapeutic agent against and through delivery sheath 22, causing momentary, isolated pressure increases. In either event, the sheath is maintained against the tissue, protecting the tissue from contact with blood.

Figure 7:
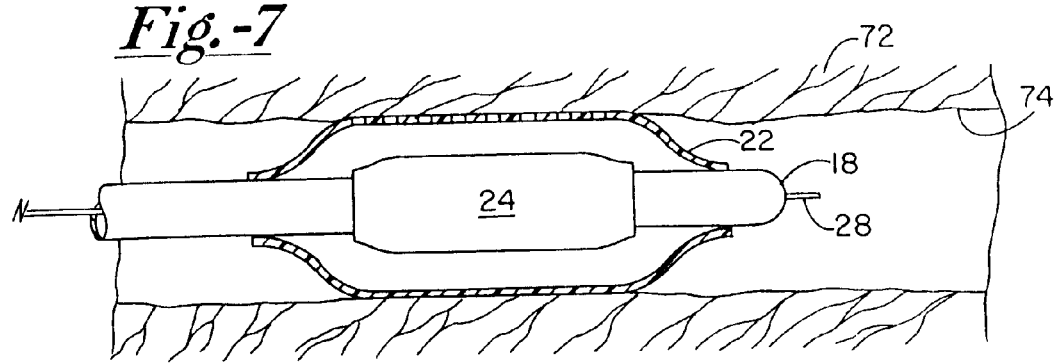

Immediately after the tissue dilatation, the dilatation fluid is withdrawn, evacuating dilatation balloon 24 to radially contract it as shown in FIG. 7. At the same time, the supply of the therapeutic agent is maintained. Thus, delivery sheath 22 remains in the expanded state against the arterial tissue, contact with blood is prevented, the therapeutic agent continues to be supplied to the tissue, and the supply of agent within compartment 52 is continually replenished through lumen 66. In this fashion, the therapeutic agent is administered until the intended treatment time has elapsed. Frequently the desired time for treatment is five minutes or more, and also involves the perfusion of blood through holes 60 and the distal portion of lumen 58.

After the drug has been administered the desired time, the supply of the agent is discontinued, and the syringe is used to withdraw the unused therapeutic agent from compartment 52. This decreases pressure within compartment 52, and the sheath returns to its radially contracted state due to the aspiration under a residual elastic force. Then catheter 20 is proximally withdrawn. The contracted delivery balloon tends to confine dilatation balloon 24, facilitating proximal withdrawal of the catheter.

As previously noted, the preferred materials for delivery sheath 22 have relatively low elastic moduli. FIGS. 8 and 9 show that an increased resiliency in the delivery sheath contributes substantially to the sheath's tendency to conform to the shape and contours of arterial tissue. The mounting of sheath 22 completely independently of dilatation balloon 24 also contributes substantially to this conformity.

FIG. 8 schematically illustrates a wall segment 76 of a non-distensible balloon 78 expanded against an arterial wall 80 which includes nodules 82 and depressions 84 between the nodules. As the balloon wall segment is pushed against the arterial tissue, there is virtually no tendency to conform to the nodules or the depressions. Rather, the balloon wall segment tends to deform the tissue, e.g. by partially flattening the nodules.

In contrast, a wall segment 86 of sheath 22 (FIG. 9) is highly flexible. Wall segment 86 does not tend to flatten or otherwise deform nodules 82. Rather, the wall portion segment elastically elongates, conforming to the nodules and entering the depressions.

Several performance advantages arise from the greater elasticity and resulting conformity to the tissue. First, wall segment 86 and the arterial tissues are contiguous over a much greater surface area. As a result a fluid tight seal is formed over the sheath/tissue interface, preventing blood from contacting tissue that is contiguous with the sheath. The prevention of contact with blood, particularly as to freshly cracked lesions, may considerably reduce the probability of restenosis.

Second, the seal enhances concentration of the therapeutic agent along the interface, more specifically that portion of the sheath/tissue interface where pores 56 are formed through the sheath. Improved concentration reduces the amount of the agent needed for effective treatment, and reduces potential toxicity concerns.

Third, the fluid tight seal effectively isolates the therapeutic agent and blood from one another, preventing the loss of efficacy in certain agents caused by contact with blood.

With the delivery sheath and tissue contiguous over a much greater proportion of their interface as in FIG. 9, the therapeutic agent perfuses through pores 56 directly into tissue, as opposed to merely perfusing into gaps between the balloon and tissue as would be the case in FIG. 8. The result is a more uniform application of the therapeutic agent to tissue under treatment. Finally, on a larger scale than that depicted in FIGS. 8 and 9, the elastic delivery sheath can conform to non-cylindrical arterial passageways, for example in regions of the coronary artery with collateral arteries, branching or eccentric lesions. The highly flexible delivery sheath can establish fluid tight seals in such areas, where the conventional non-distensible balloon does not "fit".

The administration of the therapeutic agent while dilatation balloon 24 is evacuated (FIG. 7) improves the therapy in several respects, as compared to prior arrangements in which the dilatation balloon must be inflated to force the therapeutic agent radially outward through a perforated delivery balloon. First, the flow rate of therapeutic agent through the sheath is more effectively controlled by direct control of the fluid pressure of the therapeutic agent, rather than indirect control through expansion of the dilatation balloon. The much lower pressures at which the agent is administered improve control and avoid arterial wall damage from "jetting". Secondly, the evacuated dilatation balloon occupies less space within compartment 52, leaving a larger proportion of the compartment volume occupied by the therapeutic agent. This results in more uniform fluid pressure (of the agent) throughout compartment 52, and avoids unwanted localized contact of the dilatation balloon with radially inward portions of the sheath. This leads to a more uniform flow of the agent through the sheath into tissue.

A variety of lumen configurations may be employed in lieu of the arrangement shown in FIGS. 2 and 3. FIG. 10 illustrates a concentric arrangement in which a central lumen 58a accommodates a guidewire. A dilatation fluid lumen 62a surrounds the central lumen, and in turn is surrounded by a drug delivery lumen 62a.

In FIG. 11, a guidewire lumen 58b runs through an inner catheter 59, contained within a drug delivery lumen 66b of an outer catheter 61. A dilatation fluid lumen 62b is formed within the wall of the outer catheter.

FIG. 12 shows a bundled catheter arrangement in which an outer case or catheter 63 contains three catheters: a catheter 65 containing a guidewire lumen 58c; a catheter 67 containing a dilatation fluid 62c; and a catheter 69 containing a drug delivery lumen 66c.

FIG. 13 shows the distal end region of an alternative embodiment intraluminal treatment device 88. The device includes a flexible catheter 90, and a delivery sheath in the form of a membrane 92 fused to the catheter at proximal and distal neck regions 94 and 96. Suitable membrane materials include ePTFE, collagen, silicone, and polyurethane. The catheter has a flexible distal tip 98 that protrudes beyond membrane 92. The membrane performs the same function as delivery sheath 22, but is somewhat different in structure, in that it has a natural porosity. Accordingly there is no need to form separate pores through the membrane, such as pores 56 in FIG. 2. Just as the diameter of pores 56 is selected to achieve a predetermined perfusion rate at a given fluid pressure, a material with a desired pore size can be selected for membrane 92. The membrane can have the flexibility discussed above in connection with sheath 22. At the same time, certain porous materials (e.g. collagen) lack this degree of elasticity. In such cases, membrane 92 is formed sufficiently thin (thickness up to about 0.002 inches) to achieve the requisite conforming contact with surrounding tissue. Advantages of membrane 92 include the inherent uniformity of the naturally occurring pores and the elimination of the pore-forming step in manufacturing the device. At the same time, a primary advantage of delivery sheath 22 is the ability to confine the pores to a medial region of a sheath. In any event, catheter 90 includes a drug delivery lumen open to a compartment 100 inside the membrane, as indicated at 102. The complete system includes a syringe or other source of the therapeutic agent coupled to the drug delivery lumen at the proximal end of catheter 90.

A dilatation member 104 is fixed to catheter 90 at a proximal end 106 and slidably coupled to the catheter at a distal end 108. Dilatation member 104 is a woven or braided mesh structure, radially expandable and contractible in response to axial movement of distal end 108 relative to the catheter. The dilatation member can be composed of strands having resilience and structural integrity, e.g. of spring steel, biased so that member 104 normally (i.e. when not subject to external stress) assumes a reduced-radius axially elongated state, not shown, in which distal end 108 is nearer to distal tip 98 than it appears in FIG. 13. A control wire 110 attached to distal end 108 extends proximally to an opening 112 and into a control wire lumen that extends to the proximal end of the catheter. Thus, by applying tension to control wire 110 at the proximal end of the catheter, distal end 108 is moved proximally along the catheter to radially expand and axially shorted dilatation member 104. The release of control wire 110 allows dilatation member 104 to return to the reduced radius and increased length, under its elastic restoring force.

Thus, there is no need for a source of dilatation fluid. Rather, dilatation member 104 is expanded by pulling control wire 110 to effect radial expansion, until member 104 acts through membrane 92 to dilatate surrounding tissue.

Device 88 is used in essentially the same manner as device 16, with the differences being that tensioning the control wire replaces supplying dilatation fluid to a dilatation balloon, and the subsequent release of the control wire replaces balloon aspiration. The mesh structure allows the free flow of fluids into and out of dilatation member 104. Consequently the therapeutic agent occupies substantially the entire chamber at a uniform fluid pressure. At the same time, membrane 92 must be of sufficient length to surround the axially elongated dilatation member. As it is radially expanded, the dilatation member axial center is moved proximally relative to the membrane to shift the axial alignment of the membrane and dilatation member.

Catheter 90 also incorporates a guidewire lumen, and further can incorporate a perfusion lumen or passage (e.g. lumen 58) to allow passage of blood, similar to that illustrated in the embodiment of FIGS. 2–3, during extended applications of the therapeutic agent as illustrated in FIG. 14.

Thus in accordance with the present invention, a single device is intraluminally positionable to achieve tissue dilatation and administer a therapeutic agent. The therapeutic agent is delivered by perfusion through a delivery balloon or membrane formed of a highly elastic material and mounted independently of the dilatation structure. Consequently, the balloon or membrane is expandable radially into an intimate and conforming contact against vascular tissue. The resulting seal prevents blood from entering the interface of the balloon or membrane with tissue, to protect the tissue and therapeutic agent and confine perfusion of the therapeutic agent to the intended treatment area. As a result, the likelihood of restenosis due to the blood contacting tissue is considerably reduced, and genetically engineered agents that lose their efficacy upon contact with blood can be employed with greater success.

What is claimed is:

1. A body insertable device for treatment of a treatment site in a body lumen comprising:

an elongate delivery catheter including an elongated catheter shaft having a proximal end region and a distal end region;

a treatment sheath formed of an elastic material and expandable radially into a substantially conforming contact with surrounding tissue at the treatment site, said sheath while elastically expanded cooperating with the delivery catheter to form a compartment for containing a treatment fluid, the sheath further being adapted to allow passage of the treatment fluid from within the compartment to the surrounding tissue in the body lumen;

a tissue dilator formed of a mesh dilator sheath disposed between the treatment sheath and a portion of the delivery catheter shaft;

an elongated control rod coupled to the dilator sheath to radially expand and contract the dilator sheath from a reduced radius for insertion to a radially enlarged state to press against the surrounding tissue to effect a dilatation of the surrounding tissue;

means for expanding the treatment sheath independently from the expansion of the tissue dilator; and a lumen extending along at least a portion of the catheter shaft and fluidly coupled to the compartment to supply treatment fluid to the compartment.

2. The device of claim 1 wherein: said treatment sheath is formed of a biocompatible elastomeric material.

3. The device of claim 2 wherein: said biocompatible elastomeric material consists essentially of at least one of the following: latex, urethane, silicone, and a thermoplastic elastomer.

4. The device of claim 2 wherein: the biocompatible elastomer has a modulus of elasticity in the range of 2,000 to 80,000 psi, said treatment sheath has a uniform thickness in the range of 0.5–5 mils, whereby the treatment sheath elastically expands into said substantially conforming contact with the surrounding tissue.

5. The device of claim 2 wherein: said biocompatible elastomeric material is porous.

6. The device of claim 5 wherein: said treatment sheath has a uniform thickness of at most about 2.0 mils.

7. The device of claim 2 wherein: said biocompatible elastomeric material is substantially impervious to fluids, and wherein multiple pores having diameters in a range of 15–100 microns are formed through the treatment sheath to allow said passage of the treatment fluid.

8. The treatment device of claim 1 wherein the dilator sheath is formed of a metal material.

9. A body insertable device for treatment of a treatment site in a body lumen comprising:

an elongate delivery catheter including an elongated catheter shaft having a proximal end region and a distal end region;

a treatment sheath mounted to the catheter shaft and formed of an elastic material and expandable radially into a substantially conforming contact with surrounding tissue at the treatment site, said sheath while elastically expanded cooperating with the delivery catheter to form a compartment for containing a treatment fluid, the sheath further being adapted to allow passage of the treatment fluid from within the compartment to the surrounding tissue in the body lumen;

a tissue dilator formed of a mesh sheath coupled to the catheter and disposed between the treatment sheath and a portion of the delivery catheter shaft and an elongated control rod coupled to the dilator sheath to radially expand and contract the dilator sheath from a reduced radius for insertion to a radially enlarged state to press against the surrounding tissue through the sheath to effect a dilatation of the surrounding tissue and in the radially enlarged state, a radially enlarged portion of the dilator sheath forming a portion of the compartment for containing treatment fluid for delivery through the treatment sheath;

a lumen extending along a length of the catheter shaft and fluidly coupled to the compartment to supply treatment fluid to the compartment; and a perfusion passage through the catheter shaft on opposite sides of the treatment sheath to allow a flow of body fluids within the body lumen through the catheter shaft while the treatment sheath is radially expanded.

10. A body insertable device for treatment of a treatment site in a body lumen comprising:

an elongate delivery catheter including an elongated catheter shaft having a proximal end region and a distal end region;

a treatment sheath including a proximal end and a distal end and the proximal end of the treatment sheath fixed to the catheter shaft at a first shaft connection and the distal end of the treatment sheath fixed to the catheter shaft at a second shaft connection spaced from the first shaft connection-and formed of an elastic material and expandable radially into a substantially conforming contact with surrounding tissue at the treatment site, said sheath while elastically expanded cooperating with the delivery catheter to form a compartment for containing a treatment fluid, said treatment sheath surrounds the dilator sheath and is fixed to the catheter shaft at the first and second shaft connection via fluid tight sheath couplings on opposite sides of the dilator sheath and spaced apart from the dilator sheath, the sheath further being adapted to allow passage of the treatment fluid from within the compartment to the surrounding tissue in the body lumen;

a tissue dilator formed of a mesh dilator sheath coupled to the catheter shaft and disposed between the treatment sheath and a portion of the delivery catheter shaft and an elongated control rod coupled to the dilator sheath to radially expand and contract the dilator sheath from a reduced radius for insertion to a radially enlarged state to press against the surrounding tissue through the sheath to effect a dilatation of the surrounding tissue and in the radially enlarged state, a radially enlarged portion of the dilator sheath forming a portion of the compartment for containing treatment fluid for delivery through the treatment sheath; and a lumen extending along a length of the catheter shaft and fluidly coupled to the compartment to supply treatment fluid to the compartment.

11. A body insertable device for treatment of a treatment site in a body lumen comprising:

an elongate delivery catheter including an elongated catheter shaft having a proximal end region and a distal end region;

a treatment sheath formed of an elastic material and expandable radially into a substantially conforming contact with surrounding tissue at the treatment site, said sheath while elastically expanded cooperating with the delivery catheter to form a compartment for containing a treatment fluid, the sheath further being adapted to allow passage of the treatment fluid from within the compartment to the surrounding tissue in the body lumen;

a tissue dilator formed of a mesh dilator sheath coupled to the catheter shaft and disposed between the treatment sheath and a portion of the delivery catheter shaft;

an elongated control rod coupled to the dilator sheath to radially expand and contract the dilator sheath from a reduced radius for insertion to a radially enlarged state to press against the surrounding tissue to effect a dilatation of the surrounding tissue, wherein the dilator sheath is expandable separately from the treatment sheath;

a lumen extending along a length of the catheter shaft and fluidly coupled to the compartment to supply treatment fluid to the compartment; and a guidewire lumen extending along a length of the catheter shaft to accommodate a guidewire.

12. A body insertable device comprising:

an elongated catheter shaft having a proximal end and a distal end;

a treatment sheath including a plurality of pores and a proximal end and a distal end and the proximal end fixed to the catheter shaft at a first shaft connection and the distal end fixed to the catheter shaft at a second shaft connection spaced from the first shaft connection to form a compartment for treatment fluid;

a lumen extending along a length of the catheter shaft and opened to the compartment formed by the treatment sheath;

a dilatation sheath formed of a mesh material and coupled to the catheter shaft between the treatment sheath and a portion of the catheter shaft; and means for radially expanding the dilatation sheath from a collapsed profile independently from expansion of the treatment sheath.

13. The body insertable device of claim 12 wherein the treatment sheath is formed of an elastomeric material.

14. The body insertable device of claim 13 wherein the elastomeric material is one of a latex, urethane, silicone or a thermoplastic elastomer.

15. The body insertable device of claim 12 wherein the catheter shaft includes a guidewire lumen adapted to slidably receive a guidewire.

16. A body insertable device comprising:

an elongated catheter shaft having a proximal end and a distal end;

a treatment sheath including a plurality of pores coupled to the catheter shaft to form a compartment for treatment fluid;

a lumen extending along a length of the catheter shaft and opened to the compartment formed by the treatment sheath;

a dilatation sheath formed of a mesh material and coupled to the catheter shaft between the treatment sheath and a portion of the catheter shaft and the dilation sheath being radial expandable from a collapsed profile by a control rod coupled thereto; and a perfusion passage through the catheter shaft between a proximal end and a distal end of the treatment sheath.

17. A body insertable device comprising:

an elongated catheter shaft having a proximal end and a distal end;

an expandable treatment sheath fixed to the catheter shaft at proximal and distal connections to form a treatment sheath compartment and including means for passage of fluid from the compartment to a body vessel;

a lumen extending along a length of the catheter shaft and opened to the compartment formed by the treatment sheath;

an expandable dilatation sheath coupled to the catheter shaft between the treatment sheath and a portion of the catheter shaft to form a dilatation sheath compartment in a radially expanded profile and including means for allowing passage of fluid through the dilatation sheath from the treatment sheath compartment to the dilatation sheath compartment and from the dilatation sheath compartment to the treatment sheath compartment; and means for radially expanding the treatment sheath and means for independently radially expanding the dilatation sheath from a collapsed profile to the radially expanded profile.

* * * * *

UNITED STATES PATENT AND TRADEMARK OFFICE
CERTIFICATE OF CORRECTION

PATENT NO. : 6,733,474 B2
DATED : May 11, 2004
INVENTOR(S) : Richard S. Kusleika It is certified that error appears in the above-identified patent and that said Letters Patent is hereby corrected as shown below:

<u>Title page,</u>
Item [57], ABSTRACT, replace with the following:
-- A combination dilatation and drug delivery device having a flexible catheter, a drug treatment sheath mounted to a distal end region of the catheter and a dilator sheath also mounted to the catheter and contained within a compartment formed by the sheath. The sheath is radially expandable by supplying a liquid therapeutic agent to the compartment under a moderate pressure. The dilator sheath is expandable by providing an elongated control rod coupled to the dilator sheath. The treatment sheath can be formed of a highly elastic material or can be made quite thin, and in either case is mounted independently of the dilator sheath. Thus when radially expanded, the treatment sheath is moved into a conforming contact with surrounding vascular tissue. The conforming contact protects tissue and the therapeutic agent from exposure to blood, and more effectively confines the therapeutic agent to the intended treatment area. The treatment sheath either is naturally porous or is provided with multiple pores, whereby the therapeutic agent perfuses through the treatment sheath into the surrounding tissue. --.

<u>Column 1,</u>
Line 30, change "anti-thrombolitic" to -- anti-thrombolytic --.
Lines 38-39, change "inflating spaced apart proximal and distal balloons against arterial walls" to -- inflating balloons that are proximally and distally spaced apart so that the balloons are against the arterial wall --.

<u>Column 2,</u>
Lines 51-52, change "containing at treatment fluid." to -- containing the treatment fluid. --.

UNITED STATES PATENT AND TRADEMARK OFFICE
CERTIFICATE OF CORRECTION

PATENT NO. : 6,733,474 B2
DATED : May 11, 2004
INVENTOR(S) : Richard S. Kusleika It is certified that error appears in the above-identified patent and that said Letters Patent is hereby corrected as shown below:

<u>Column 4,</u>
Line 40, change "Consequently the" to -- Consequently, the --.
Line 43, change "Thus in accordance" to -- Thus, in accordance --.

<u>Column 9,</u>
Line 14, change "62a" to -- 66a --.

Signed and Sealed this

Twenty-fifth Day of April, 2006

JON W. DUDAS
*Director of the United States Patent and Trademark Office*